United States Patent [19]
Zupkas

[11] Patent Number: 5,935,125
[45] Date of Patent: Aug. 10, 1999

[54] FULGURATION AND CAUTERIZATION DEVICE

[75] Inventor: Paul F. Zupkas, San Diego, Calif.

[73] Assignee: Uros Corporation, San Diego, Calif.

[21] Appl. No.: 08/634,067

[22] Filed: Apr. 17, 1996

[51] Int. Cl.[6] .................................................. A61B 17/39
[52] U.S. Cl. ............................... 606/46; 606/45; 606/41; 606/46; 606/49
[58] Field of Search ................................ 606/40–42, 45, 606/46, 48–50; 128/642; 600/373, 156

[56] References Cited

U.S. PATENT DOCUMENTS

| | | |
|---|---|---|
| D. 320,446 | 10/1991 | Grossi et al. . |
| 4,719,914 | 1/1988 | Johnson . |
| 4,917,082 | 4/1990 | Grossi et al. . |
| 4,936,842 | 6/1990 | D'Amelio et al. . |
| 5,085,655 | 2/1992 | Ben-Simbon . |
| 5,160,334 | 11/1992 | Bilings et al. . |
| 5,190,541 | 3/1993 | Abele et al. .............................. 606/46 |
| 5,195,959 | 3/1993 | Smith . |
| 5,224,944 | 7/1993 | Elliott . |
| 5,242,442 | 9/1993 | Hirschfeld . |
| 5,267,994 | 12/1993 | Gentelia et al. . |
| 5,312,400 | 5/1994 | Bales et al. . |
| 5,318,565 | 6/1994 | Kuriloff et al. . |
| 5,348,555 | 9/1994 | Zinnanti . |
| 5,354,296 | 10/1994 | Turkel ...................................... 606/49 |
| 5,360,427 | 11/1994 | Majlessi . |
| 5,395,363 | 3/1995 | Billings et al. ........................... 606/45 |
| 5,437,665 | 8/1995 | Munro . |
| 5,451,222 | 9/1995 | De Maagd et al. . |
| 5,549,605 | 8/1996 | Hahnen .................................... 606/49 |
| 5,634,924 | 6/1997 | Turkel et al. ............................. 606/45 |
| 5,658,280 | 8/1997 | Issa .......................................... 606/46 |

*Primary Examiner*—Jack W. Lavinder
*Assistant Examiner*—David Ruddy
*Attorney, Agent, or Firm*—Knobbe, Martens, Olson & Bear, LLP

[57] ABSTRACT

A wire frame made of conductive material has a proximal end and a distal end. The wire frame is adapted for receiving an electrical potential from a remote power source. A loop of wire is disposed at the distal end of the wire frame, and a roller is disposed between the proximal end of the wire frame and the loop of wire. The wire frame is insulated, with the exception of the loop of wire and a portion of the wire frame contacting the roller. A source of suction adapted for removing gases from an area within the vicinity of the roller is activated when the electric potential is applied to the wire frame and the roller is placed in contact with human or animal tissue to thereby perform fulguration thereon. The source of suction is adapted to be reversed in order to provide a positive flow of fluid onto the roller, when the electrical potential is not applied to the wire frame.

6 Claims, 2 Drawing Sheets

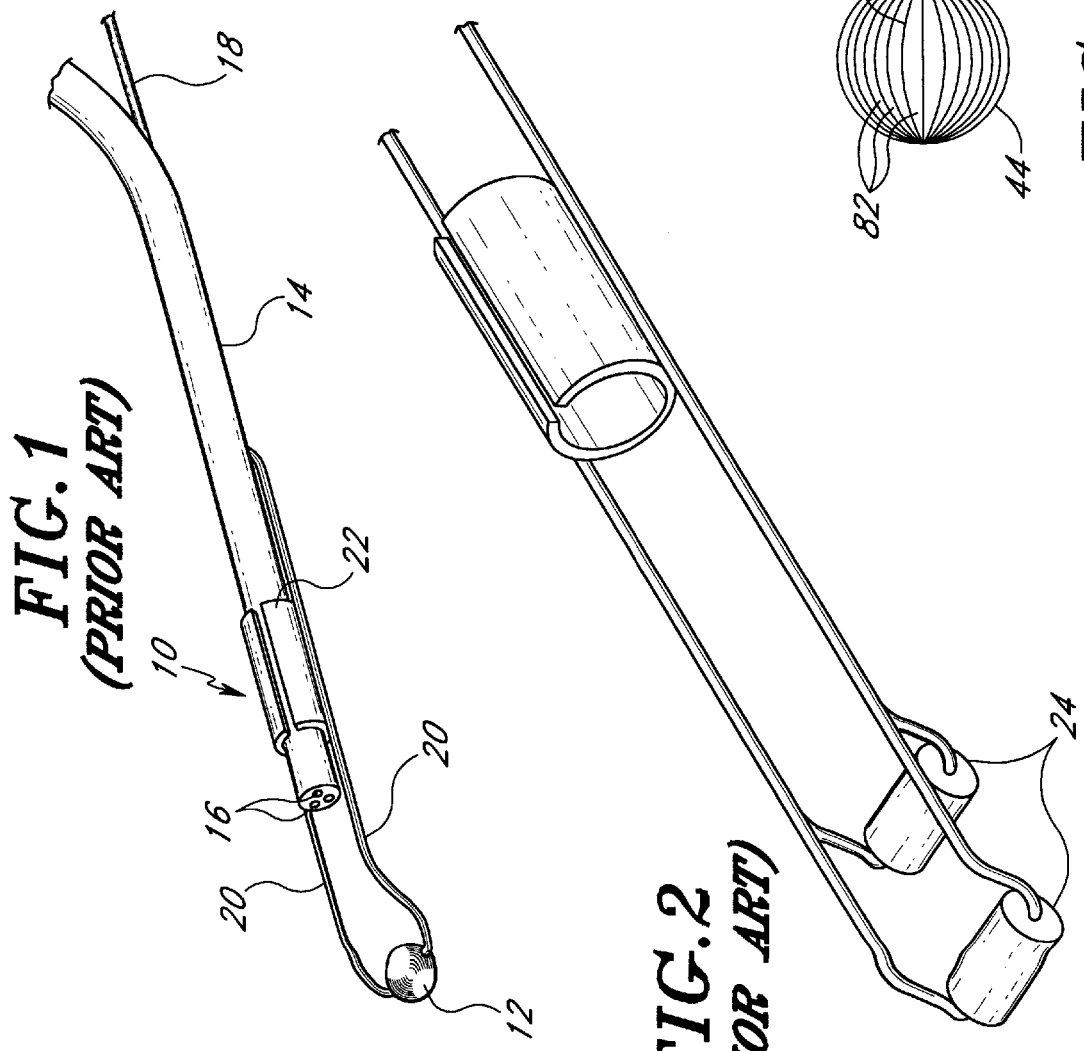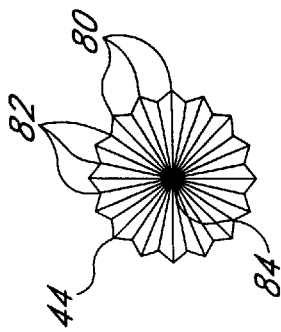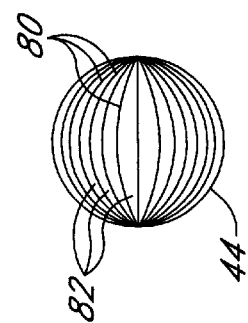

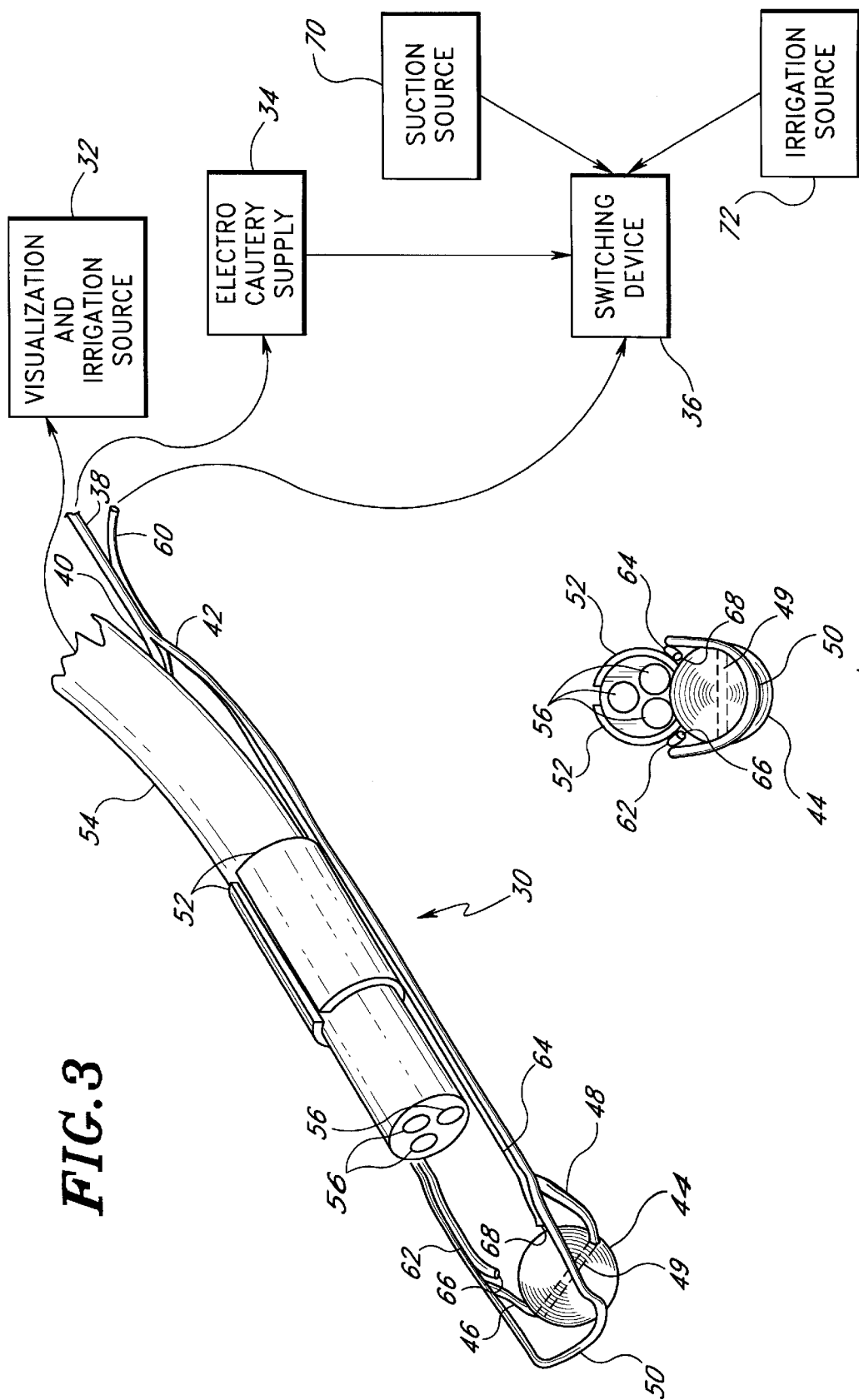

FULGURATION AND CAUTERIZATION DEVICE

BACKGROUND OF THE INVENTION

1. Field of the Invention

The present invention relates generally to apparatuses using electricity to cut or vaporize tissue and, more particularly, to an apparatus having both an electrically charged roller and an electrically charged loop for performing fulguration and cauterization.

Benign prostatic hyperplasia is a medical condition where growth of the prostate gland results in a partial occlusion of the lumen of the urethra. The occlusion of the lumen from this benign growth results in a greater pressure requirement for the patient to void, increased frequency of urination, and greater urine retention in the bladder.

One prior art approach for ablating tissue within the lumen of the urethra involves placing both a resectoscope electrode and a cystoscope within the urethra. The cystoscope is used for visualization while high voltage is applied to the resectoscope electrode in order to remove the benign tissue growth from the lumen of the urethra, thus increasing lumen size, reducing the pressure required to void, and increasing the diameter of the stream of urine. This prior art procedure is conventionally referred to as a transurethral resection of the prostate. Although this procedure is somewhat effective, a shortcoming associated with this procedure is bleeding, which often necessitates one or two days of post-operative hospital time for the patient. Additionally, patients on certain types of medication that affect blood clotting abilities are either contraindicated for this medical procedure or have an increased risk due to the bleeding.

Other procedures of the prior art for treating benign prostatic hyperplasia have been developed for at least partially avoiding the problem associated with bleeding. These procedures include laser, microwave, radio frequency, and thermal abrasion. Each of these procedures presents its own set of complications and shortcomings. One prior art procedure for treating benign prostatic hyperplasia involves the ablation of prostatic tissue through vaporization using a high energy electrical current, which passes through a rollerball placed within the lumen of the urethra and into the electrically grounded patient. The procedure, which is commonly referred to as fulguration, can be implemented using the prior art apparatus illustrated in FIG. 1. The insulated probe 10 comprises a partially insulated metallic structure, a conducting rollerball 12, and a cylindrical housing 14. Electric current is supplied to the conducting rollerball 12 from a power source through the proximal end 18 of insulated wire, and through two insulated wires 20.

The two insulated wires 20 are joined together by a non-insulated portion of wire, which forms an axis of rotation for the conducting rollerball 12. When the electrical current is applied to the conducting roller ball 12 via the proximal end 18, irrigation fluid is delivered from the cylindrical housing 14 via one of the apertures 16. One of the other two apertures 16 typically accommodates an optical fiber for viewing the ablative site, while the remaining aperture 16 accommodates a light source optical fiber. Electrical current supplied to the conducting rollerball 12 arcs from the conducting rollerball 12 into the tissue within the urethra that comes into contact with the conducting rollerball 12. The electrical spark from the conducting rollerball 12 to the tissue vaporizes the tissue. The irrigation fluid from the apertures 16 includes a non-ionic fluid, which is continuously flushed through the cavity and over the device during the vaporization process. The rolling motion of the conducting rollerball 12 is useful for vaporizing tissues in body cavities, such as the endometrium.

Another prior art device, illustrated in FIG. 2, is similar to the insulating probe 10 of FIG. 1, with the exception of the two cylinders 24 used in place of the conducting rollerball 12. This double cylinder design may in some instances improve ablation and keep tissue from attaching to the cylinders 24, thus increasing the efficiency of the vaporization process.

These prior art apparatuses suffer because of generation of gas caused during the ablation process, the difficulty in removing tissue flaps resulting from the ablation process, and inefficiencies in the design of the conducting rollerball or cylinder. As current passes from the conducting rollerball 12 of the apparatus of FIG. 1, or from the conducting cylinder 24 of the apparatus of FIG. 2, into the tissue to be ablated, tissue is vaporized. This vaporization of tissue presents a potential hazard, resulting from airborne viruses that may exist in gas bubbles generated by the vaporization process. Any viruses within these gas bubbles will be released into the operating room when the vaporization gas is flushed from the bladder. Gas generated from the vaporization procedure additionally obscures the surgical field, as viewed through the cystoscope. The narrow field of view provided by the cystoscope can be nearly totally obscured by the gas bubbles generated by the vaporization process. A need for a clear field of view is particularly important at the distal and proximal ends of the prostate, where urethral and bladder sphincters controlling continence are present. The surgeon may accidentally vaporize too much tissue when the limited view provided by the cystoscope is obstructed with gas bubbles. This vaporization of too much tissue may significantly damage the sphincters and result in incontinence. A need has thus existed in the prior art for an apparatus which can safely route these gas bubbles away from the field of view of the cystoscope to thereby reduce the likelihood of damaging sphincters, for example. Additionally, such a routing means should route these gas bubbles into a safe receptacle, to thereby prevent introduction of any airborne viruses into the operating room.

In addition to gas bubbles, tissue flaps created during the fulguration (ablation) process tend to obstruct the limited field of view of the cystoscope, as well. Prior art devices comprising only a conducting rollerball 12 or a conducting cylinder 24 are not able to efficiently remove these flaps of tissue, since the flaps of tissue are not anchored by surrounding tissue and have a tendency to move as they are manipulated by the rollerball or cylinder. The existence of these flaps of tissue, and the associated difficulty in removing them, results in an uneven removal of tissue by the rollerball or cylinder. Even tissue, such as the urethral sphincter, may be undesirably ablated as the result of the existence of flaps of tissue in the area. A need has thus existed in the prior art for an apparatus that can efficiently remove flaps of tissue generated during the fulguration process.

Still another problem associated with the prior art stems from intrinsic limitations in the designs of the rollerballs or cylinders of the prior art. These cylinders commonly comprise smooth surfaces, which are prone to accumulation of tissue and carbon deposits. Additionally, these smooth surfaces do not provide an optimal amount of friction and, thus, some slippage or skidding of these prior art rollers often occurs. A need has existed in the prior art for conducting rollers which have traction and which exhibit better cleaning and operating properties.

SUMMARY OF THE INVENTION

The fulguration and cauterization device of the present invention includes structure for evacuating gas bubbles from the site of ablation, to thereby increase visibility and route the gas bubbles away from ambient air within the operating room. A cutting loop is also provided, in addition to a roller assembly, for cutting flaps of tissue created during the fulguration process. Additionally, the roller of the present invention includes ridges for increasing both traction and the operating efficiency of the roller assembly.

According to one broad aspect of the present invention, a wire frame made of conductive material has a proximal end and a distal end. The wire frame is adapted for receiving an electrical potential from a remote power source. A loop of wire is disposed at the distal end of the wire frame, and a roller is disposed between the proximal end of the wire frame and the loop of wire. The wire frame is insulated, with the exception of the loop of wire and a portion of the wire frame contacting the roller. A source of suction adapted for removing gases from an area within the vicinity of the roller is activated when the electric potential is applied to the wire frame and the roller is placed in contact with human or animal tissue to thereby perform fulguration thereon. The source of suction is adapted to be reversed in order to provide a positive flow of fluid onto the roller, when the electrical potential is not applied to the wire frame.

The source of suction can be switched between a positive pressure flow and a negative pressure flow, depending on whether the electric potential is being applied to the wire frame or not being applied, respectively. In the event that the source of suction becomes clogged, for example, a positive flow may be applied to the device to thereby alleviate the clog without any necessity for removing the device from the area of surgery. A particular advantage of applying a negative pressure (suction) to remove gases from the ablation site is the resultant increased visibility. The gas bubbles tend to "stick" to the lens of the cystoscope, impairing the practitioner's ability to view the ablation site.

The roller may comprise either a sphere or a cylinder, and is adapted to perform fulguration on tissue when the electric potential is applied. The loop of wire also receives the electric potential, and is adapted for cutting flaps of tissue created during the fulguration process by the roller. The fulguration and cauterization device further includes an apparatus adapted for providing visualization of at least a portion of the rollerball. This apparatus for providing visualization may comprise a cystoscope, for example, which is positioned in a plane slightly higher than planes occupied by the loop of wire and the roller.

The roller is rotatably mounted on an axis, which is connected to the wire frame. The roller includes a plurality of grooves and ridges. Each of the grooves and ridges is parallel to the axis of rotation of the roller.

According to another broad aspect of the present invention, a fulguration and cauterization device includes a wire frame made of a conductive material and having a proximal end and a distal end. A source of irrigation and an apparatus for providing visualization to a user are provided within a cylindrical housing, which is connected to the wire frame. A rollerball is disposed between the proximal end of the wire frame and a loop of wire, and the source of suction is positioned near the rollerball. The source of suction may be switched between a positive pressure mode and a negative pressure mode, to route fluid onto the rollerball when electric potential is not applied to the wire frame and to remove fluid and gas bubbles from near the rollerball when electric potential is applied to the wire frame.

The present invention, together with additional features and advantages thereof, may best be understood by reference to the following description taken in connection with the accompanying illustrative drawings.

BRIEF DESCRIPTION OF THE DRAWINGS

FIG. 1 illustrates a first prior art fulguration device having a rollerball;

FIG. 2 illustrates a second prior art fulguration device having two cylinders;

FIG. 3 illustrates a fulguration and cauterization device according to the presently preferred embodiment;

FIG. 4 illustrates a front elevational view of the fulguration and cauterization device of the presently preferred embodiment;

FIG. 5 illustrates a front elevational view of the rollerball of the presently preferred embodiment; and FIG. 6 illustrates a side elevational view of the rollerball of the presently preferred embodiment.

DETAILED DESCRIPTION OF THE PREFERRED EMBODIMENT

Turning to FIG. 3, a fulguration and cauterization device 30, constructed in accordance with principles of the invention, is illustrated connected to a visualization and irrigation source 32, an electro-cautery supply 34, and a switching device 36. The fulguration and cauterization device 30 comprises a proximal insulated conductor 38 which forks into a first insulated conductor 40 and a second insulated conductor 42. A rollerball 44 is held between a first rollerball support arm 46 and a second rollerball support arm 48. Although the first rollerball support arm 46 and the second rollerball support arm 48 are preferably insulated, a shaft 49 running through the rollerball 44 and connecting the first rollerball support arm 46 to the second rollerball support arm 48 is preferably uninsulated. The rollerball 44 is rotationally mounted around the shaft 49 between the two rollerball support arms 46 and 48. The first rollerball support arm 46 and the second rollerball support arm 48 are connected to the first insulated conductor 40 and the second insulated conductor 42, respectively.

An uninsulated cutting loop 50 is connected between the first insulated conductor 40 and the second insulated conductor 42. The first and second insulated conductors 40 and 42, the first and second rollerball support arms 46 and 48, the rollerball 44, and the uninsulated cutting loop 50 preferably comprise a conductive material. As presently embodied, these elements are comprised of stainless steel. A support sleeve 52, which may also comprise stainless steel, holds a cylindrical housing 54. The cylindrical housing 54 preferably comprises means for providing visualization through the apertures 56, as well as for providing irrigation through the apertures 56. This cylindrical housing 54 is connected to the visualization and irrigation source 32 by conventional means.

The rollerball 44 and the uninsulated cutting loop 50 are the points of contact where current flows from the electro-cautery supply 34, through the first and second insulated conductors 40 and 42, and through the rollerball 44 into the tissue of the patient. Current also flows from the first insulated conductor 40 and the second insulated conductor 42, through the uninsulated cutting loop 50, and into the tissue of the patient.

Current flowing from the rollerball 44 into the tissue of the patient provides a fulguration effect on the tissue, and current flowing from the uninsulated loop 50 provides a cauterization effect on the tissue. In other words, the rollerball 44 tends to ablate tissue and the uninsulated cutting loop 50 tends to cut tissue. A front elevational view of the fulguration and cauterization device 30 is shown in FIG. 4. Both the rollerball 44 and the uninsulated cutting loop 50 are positioned below the cylindrical housing 54, to thereby facilitate a wider angle of view from the cystoscope connected to the visualization and irrigation source 32. The height of the uninsulated cutting loop 50, relative to the height of the rollerball 44, determines the depth of tissue cut by the uninsulated cutting loop 50. The uninsulated cutting loop 50 may be raised for a shallower cut, and may be lowered for a deeper cut. The uninsulated cutting loop 50 is particularly advantageous for removing tissue flaps generated by the fulguration process. These tissue flaps are difficult to remove, and tend to obstruct the view of the cystoscope.

Referring now to FIGS. 3 and 4, a proximal hollow tube 60 forks into a first hollow tube 62 and a second hollow tube 64. The first hollow tube 62 terminates into a first tube aperture 66, and the second hollow tube 64 terminates into a second tube aperture 68. The switching device 36 is adapted to apply either a negative pressure from the suction source 70 or a positive pressure from the irrigation source 72 to the proximal hollow tube 60. When the suction source 70 is applied to the proximal hollow tube 60, a negative pressure at the first tube aperture 66 and at the second tube aperture 68 removes fluid and gas bubbles generated by the rollerball 44, for example, during the fulguration process. Removal of fluid and gas bubbles through the first tube aperture 66 and the second tube aperture 68 serves to reduce the risk of introduction of biohazards into the operating room, and further serves to keep the surgical field clear.

When the irrigation source 72 is applied to the proximal hollow tube 60, a fluid is delivered from the first tube aperture 66 and the second tube aperture 68. The delivery of fluid to the first tube aperture 66 and the second tube aperture 68 serves to reduce the possibility of occluding these tubes with debris, such as tissue particles, blood clots, vaporization byproducts, and other matter. Thus, the first hollow tube 62 and the second hollow tube 64 are less likely to be occluded when tissue is not being vaporized and, additionally, any such occlusion may be cleared by the delivery of fluid from the irrigation source 72 through the first tube aperture 66 and the second tube aperture 68. In the presently preferred embodiment, the suction source 70 is applied to the proximal hollow tube 60 during vaporization, and the irrigation source 72 is applied to the proximal hollow tube 60 when vaporization is not occurring. If any portion of tubing between the proximal hollow tube 60 and the first and second tube apertures 66 and 68 becomes occluded during vaporization, the surgeon need only cease vaporization to thereby cause fluid to be delivered from the irrigation source 72 through the first and second tube apertures 66 and 68. Accordingly, any interruption in the fulguration due to an obstruction in the suction tube may be quickly rectified without requiring removal of the fulguration and cauterization device 30 from the operating site.

As presently embodied, the irrigation source 72 routes fluid directly onto the rollerball 44 via the first tube aperture 66 and the second tube aperture 68. As the rollerball 44 vaporizes tissue, the rollerball 44 has a tendency to develop a coating of carbonized tissue thereon. Tissue particles may adhere to this carbon layer on the rollerball 44, thereby reducing the efficiency of the vaporization process by attenuating sparks and preventing the rollerball 44 from rolling. Another advantage of the present invention is that the delivery of a jet of fluid from the first tube aperture 66 and the second tube aperture 68 to the surface of the rollerball 44 cleans the surface of the rollerball 44 by removing material therefrom. Any fluid routed from the visualization and irrigation source 32 via the apertures 56 is not likely to provide this cleaning effect on the rollerball 44, since the orientation of the apertures 56 does not lend to the routing of sufficiently high-pressured fluid onto the rollerball 44.

The first tube aperture 66 and the second tube aperture 68 are both positioned to maximize the removal of gas bubbles and, further, to deliver efficient jet streams of fluid. The positioning of these tube apertures 66 and 68 is further influenced by the need to minimize obstruction of the surgical field. The tubing between the first and second tube apertures 66, 68 and the proximal hollow tube 60 preferably comprises a material that is rigid but thin-walled to thereby provide a minimum profile. These tubes, the insulated conductors, the rollerball 44 and the uninsulated cutting loop 50 are all preferably part of an integral, disposable unit. As presently embodied, the cylindrical housing 54 is not disposable and can be reused. Other configurations of the suction and delivery system may comprise only a single tube, or may be adaptable to a single probe arm device (instead of the two arms 40, 42) or a device utilizing either a single or double cylinder instead of the rollerball 44.

The suction source 70 may comprise a simple vacuum suction source, for example, and the irrigation source 72 may comprise a pressure delivery source for delivering a known irrigation fluid, such as sterile distilled water, for example. The switching device 36 may comprise a solenoid, which is switchable between the suction source 70 and the irrigation source 72 depending on the flow of current. When current flows to the proximal insulated conductor 38, the suction source 70 is activated, and when no current flows, the irrigation source 72 is activated. The vacuum and pressure delivered by the suction source 70 and the irrigation source 72 may be regulated to control the rate of suction and delivery. The suction source 70 and the irrigation source 72 may comprise conventional vacuum and pressure lines available in a hospital, for example. The electro-cautery supply 34 may comprise a conventional electro-cautery machine. As presently embodied, the fulguration and cauterization device 30 is configured to be adaptable to any commercially available electro-cautery machine.

FIG. 5 illustrates a front elevational view of the rollerball 44, and FIG. 6 illustrates a side elevational view of this rollerball 44. The ridges 80 and grooves 82 are preferably positioned along the rollerball 44 in directions which are substantially parallel to the axis of rotation 84 of the rollerball 44. These ridges 80 and grooves 82 provide an enhanced frictional contact between the rollerball 44 and the tissue being fulguratized, and thus promote efficient rolling of the rollerball 44 over the tissue. These ridges 80 and grooves 82 provide traction to the rollerball 44 in a similar fashion to the traction provided by a tank tread, and further serve to reduce the amount of carbonization on the surface of the rollerball 44, thus optimizing the ability of the rollerball 44 to vaporize tissue.

Although an exemplary embodiment of the invention has been shown and described, many other changes, modifications and substitutions, in addition to those set forth in the above paragraph, may be made by one having ordinary skill in the art without necessarily departing from the spirit and scope of this invention.

I claim:

1. A fulguration and cauterization device, comprising:
   a frame comprising a conductive material, the frame having a proximal end and a distal end and being adapted for receiving an electrical potential from a power source;
   a roller disposed on the frame, the roller comprising a conductive material and being in electrical communication with the frame; and
   a source of suction adapted for removing gasses from an area in the vicinity of the roller, when the electric potential is applied to the frame and the roller is placed in contact with human or animal tissue to perform fulguration thereon;
   wherein the source of suction is further adapted to be reversed in order to provide delivery of a fluid;
   wherein the source of suction is activated to remove gasses when the electric potential of the power source is applied to the frame;
   wherein the source of suction is reversed to provide delivery of fluid when the electric potential is not applied to the frame;
   wherein the source of suction comprises two tubes having openings near the roller.

2. The fulguration and cauterization device according to claim 1, wherein fluid delivered by the source of suction serves to both flush the source of suction and to clean the roller, to thereby extend an amount of time that the fulguration and cauterization device may be operated continuously without removal from a surgical site.

3. A fulguration and cauterization device, comprising:
   a frame comprising a conductive material, the frame having a proximal end and a distal end and being adapted for receiving an electrical potential from a power source;
   a roller disposed on the frame, the roller comprising a conductive material and being in electrical communication with the frame;
   a source of suction adapted for removing gasses from an area in the vicinity of the roller, when the electric potential is applied to the frame and the roller is placed in contact with human or animal tissue to perform fulguration thereon; and
   a cutting loop disposed at the distal end of the frame, wherein the cutting loop is in electrical communication with the frame and the roller is disposed between the proximal end of the frame and the cutting loop;
   wherein the fulguration performed by the roller creates tissue flaps;
   wherein the cutting loop cuts and cauterizes the tissue flaps created by the roller during the fulguration process.

4. A fulguration and cauterization device, comprising:
   a frame comprising a conductive material, the frame having a proximal end and a distal end;
   a wire disposed at the distal end of the frame wherein the wire is in electrical communication with the frame;
   a roller disposed on the frame, the roller comprising a conductive material and being in electrical communication with the frame and the roller is disposed between the proximal end of the frame and the wire; and
   a power source adapted for applying an electric potential to the frame;
   wherein the roller comprises one of a sphere and a cylinder, and is adapted to perform fulguration on a portion of tissue;
   wherein the wire comprises a loop of wire that is adapted for performing cauterization on a portion of tissue;
   wherein the fulguration performed by the roller creates tissue flaps; and
   wherein the loop of wire cuts and cauterizes the tissue flaps created by the roller during the fulguration process.

5. The fulguration and cauterization device according to claim 4, wherein the fulguration and cauterization device is adapted to be inserted into a body cavity.

6. A fulguration and cauterization device, comprising:
   a frame comprising a conductive material, the frame having a proximal end and a distal end;
   a wire disposed at the distal end of the frame;
   a roller adapted to perform fulguration on a portion of tissue disposed on the frame, the roller comprising a conductive material and being in electrical communication with the frame and the roller is disposed between the proximal end of the frame and the wire; and
   an apparatus adapted for providing visualization of at least a portion of the roller to a user;
   wherein the apparatus adapted for providing visualization of the wire to a user comprises a cystoscope;
   wherein a horizontal plane passing through a central area of the cystoscope is above a plane passing through a central area of the roller.

* * * * *